(12) United States Patent
Zheng et al.

(10) Patent No.: US 8,118,818 B2
(45) Date of Patent: Feb. 21, 2012

(54) METHOD AND DEVICE FOR COMPUTER ASSISTED DISTAL LOCKING OF INTRAMEDULLARY NAILS

(75) Inventors: Guoyan Zheng, Bern (CH); Xuan Zhang, Bern (CH)

(73) Assignee: AO Technology AG, Chur (CH)

( * ) Notice: Subject to any disclaimer, the term of this patent is extended or adjusted under 35 U.S.C. 154(b) by 792 days.

(21) Appl. No.: 12/279,409

(22) PCT Filed: Dec. 15, 2006

(86) PCT No.: PCT/CH2006/000704
§ 371 (c)(1),
(2), (4) Date: Oct. 21, 2008

(87) PCT Pub. No.: WO2008/071014
PCT Pub. Date: Jun. 19, 2008

(65) Prior Publication Data
US 2009/0054910 A1    Feb. 26, 2009

(51) Int. Cl.
*A61B 19/00* (2006.01)
(52) U.S. Cl. ...................................................... 606/130
(58) Field of Classification Search .................. 606/130, 606/102; 600/407, 425–429, 417, 431–435; 378/21, 25, 26, 205, 206
See application file for complete search history.

(56) References Cited

U.S. PATENT DOCUMENTS

| | | | |
|---|---|---|---|
| 6,942,385 B2 * | 9/2005 | Fadler et al. | 378/205 |
| 7,050,845 B2 * | 5/2006 | Vilsmeier | 600/427 |
| 2005/0027304 A1 | 2/2005 | Leloup et al. | |
| 2011/0213379 A1 * | 9/2011 | Blau et al. | 606/102 |

FOREIGN PATENT DOCUMENTS

| | | |
|---|---|---|
| WO | 00/47103 | 8/2000 |
| WO | 02/37935 | 5/2002 |
| WO | 03/043485 | 5/2003 |
| WO | 2005/000129 | 1/2005 |

* cited by examiner

*Primary Examiner* — Kevin T Truong
(74) *Attorney, Agent, or Firm* — Rankin, Hill & Clark LLP

(57) ABSTRACT

A method and a device for computer assisted distal locking of intramedullary nails comprising the steps of: A) establishing a virtual geometric representation of an intramedullary nail (1); B) acquiring a first medical image (28) using a radioscopic unit (25) with its focal line (23) adjusted at an angle between 0° and 30° to the axis (8,9) of the at least one distal locking hole (3,4); C) acquiring a second medical image using a radioscopic unit (25) with its focal line (23) adjusted at an angle between 60° and 90° to the axis (8,9); D) computing the position of the longitudinal axis (2) of the distal part (5) of the intramedullary nail (1) using said first and second medical image and said virtual geometric representation by means of a computer (40); E) computing the position of the axis (8,9) of the at least one distal locking hole (3,4) using said first and second medical image (28,29); F) transferring information related to the positions of the distal part (5) and the at least one distal locking hole (3,4) from a central processing unit of the computer (40) to an external guide means (41) for drilling a hole in a bone (30).

5 Claims, 4 Drawing Sheets

METHOD AND DEVICE FOR COMPUTER ASSISTED DISTAL LOCKING OF INTRAMEDULLARY NAILS

FIELD OF THE INVENTION

The invention relates to a method for computer assisted distal locking of intramedullary nails according to the preamble of claim 1.

Femoral shaft fractures are one of the most common injuries encountered in clinical routine trauma surgery. Mostly the bone fragments are displaced and need to be surgically reduced. Intramedullary nailing with or without previous reaming of the intramedullary channel is an excellent operative procedure in treatment of fractures of the femoral shaft. The surgical procedure involves the fixation of the long-bone fractures by inserting an intramedullary nail, which is prefabricated into the intramedullary channel of the fractured bone. The surgeon inserts the implant by:
- making an incision in the proximal femur;
- reducing the bone fragments;
- inserting the intramedullary nail through the fragments; and
- finally locking the intramedullary nail with transverse screws to establish a means for internal support of the bone fragments.

The transverse interlocking screws are essential to control the rotation and translation of the bone fragments with respect to each other. In comminuted fractures, these interlocking screws also bear the transmitted load until the fractures has consolidated. To insert the transverse interlocking screws it is necessary to align the drill bit and drill through the bone to meet the proximal and distal interlocking screw opening in the intramedullary nail.

DESCRIPTION OF THE PRIOR ART

A method for computer assisted distal locking of intramedullary nails is known from US 2005/0027304 LELOUP. The method disclosed includes the steps of:
- acquiring two medical images of the distal part of an intramedullary nail, one approximately medio-lateral and one approximately antero-lateral; and
- matching the distal part including the distal locking holes projected onto the two medical images with a virtual geometric representation of the distal part of the intramedullary nail, whereby the virtual geometric representation of each distal locking hole simply consists of a right circular cylinder with an axis perpendicular to the longitudinal axis of the intramedullary nail. The disadvantage of this known method is that only the determination of the position of the distal part of the intramedullary nail is based on both medical images while for the determination of the position of the distal locking holes only the information of the medio-lateral image is used. The simplified virtual geometric representation used for the distal locking holes prevents from using the information provided by the antero-lateral image.

SUMMARY OF THE INVENTION

It is an object of the invention to provide a method for computer assisted distal locking of intramedullary nails which allows to improve the accuracy of position determination of the distal locking holes of an intramedullary nail and the robustness of the iterative procedure with regard to its convergence.

The invention solves the posed problem with a method for computer assisted distal locking of an implanted intramedullary nail according to the subject of claim 1 and with a device for computer assisted distal locking of an implanted intramedullary nail according to the subject of claim 5.

One of the advantages of the present invention is that due to the use of both images—the medio-lateral and the antero-posterior image—the accuracy of the determination of the position of the distal locking holes and the robustness of the iterative procedure with regard to its convergence can be improved. It works even well when there are contours of surgical instruments and/or cables projected onto the medical images.

In a preferred embodiment the external guide means is a computer display such allowing the advantage that a common surgical navigation system may be used with visual guidance for the surgeon to manually drill the hole.

In a further embodiment the external guide means is a computer controlled drive for automatically adjusting a drill guide. This embodiment shows the advantage that a mechanical device for guiding the drilling device is but the surgeon may manually drill the hole under visual and haptic control.

In another embodiment the external guide means is a surgical roboter automatically drilling the hole in the bone. This embodiment has the advantage of a completely automatic process for drilling the holes in the bone necessary to interlock the intramedullary nail by means of bone screws.

A BRIEF DESCRIPTION OF THE DRAWINGS

The preferred embodiment of the invention will be described in the following by way of example and with reference to the accompanying drawings in which.

Figure 1:
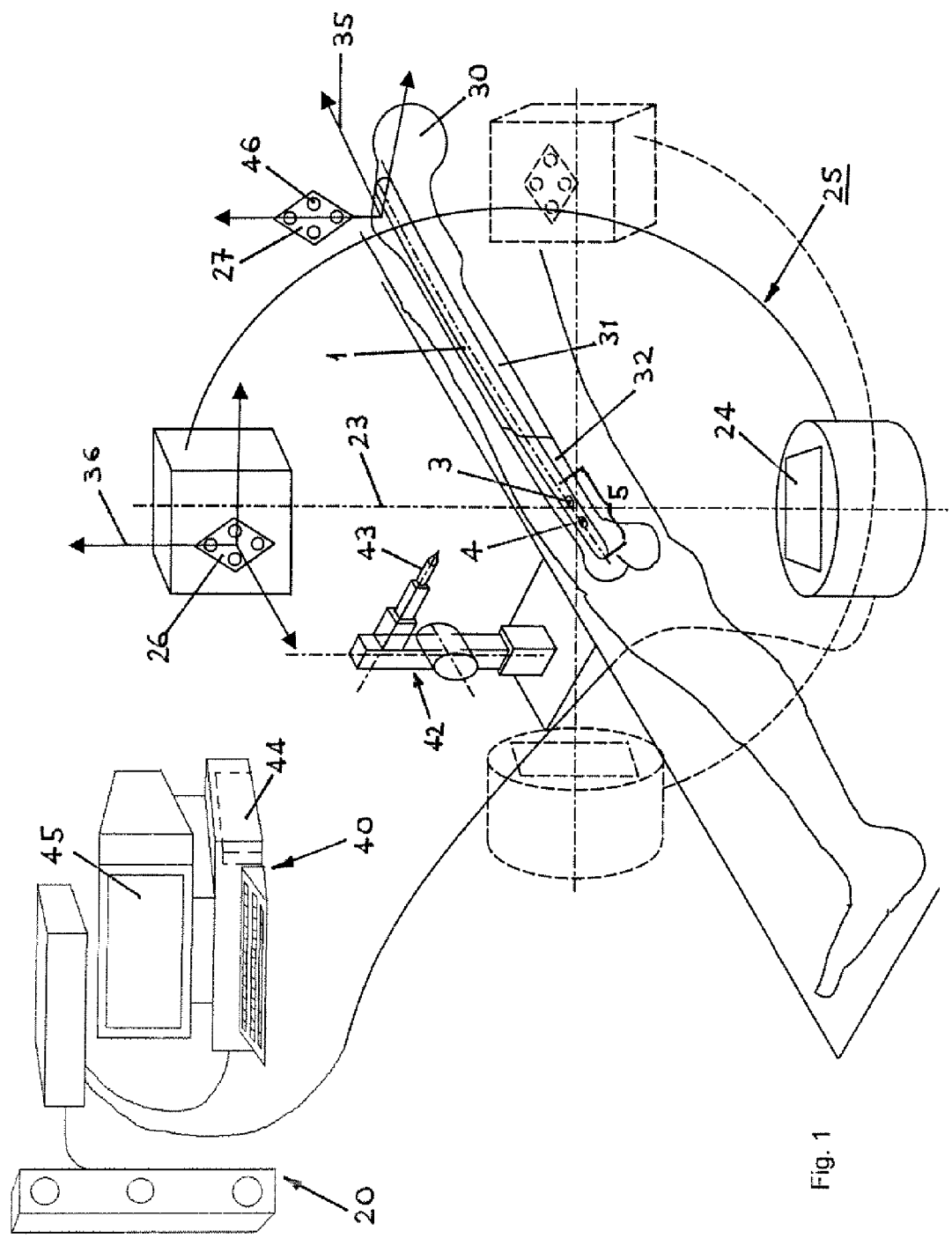
FIG. 1 illustrates a perspective view of an embodiment of the device according to the invention.

An embodiment of the device for computer assisted distal locking of an intramedullary nail is illustrated in FIG. 1, said device comprising:
a) a computer 40 with a data store 44 and a display 45 and being suitably programmed to perform the computing steps according to the method according to the invention, such allowing to determine the position of the distal part 5 as well as of the first and second distal locking hole 3, 4 of an intramedullary nail 1 which is inserted in the medullary channel of a bone 30, e.g. a femur;

b) a position measurement device 20 electronically connected to the computer 40 for measuring the position of the markers 46 attached to a first and a second reference element 26, 27;

c) a radioscopic unit 25 with a focal line 23 and the first reference element 26 attached thereto, said radioscopic unit 25 allowing to acquire a first and second medical image 28, 29 (FIGS. 4 and 5) of at least a distal part 5 of an intramedullary nail 1 including at least a first and a second distal locking hole 3,4 with an axis 8, 9 (FIG. 2) each, said first and second medical image 28, 29 being acquired with the focal line 23 being transverse to the intramedullary nail 1 and with the focal line 23 adjusted at an angle between 0° and 30° to the axes 8, 9 of the first and second distal locking hole 3, 4, respectively at an angle between 60° and 90° to said axes 8, 9 for the second medical image 29;

d) a second reference element 27 connected with the intramedullary nail 1 or with a bone 30 in which the intramedullary nail 1 is implanted;

e) a roboter 42 comprising a drill bit 43 with a central axis allowing to drill holes necessary for the distal locking of an intramedullary nail 1. The position of said holes are previously calculated by means of said computer 40 through referencing the first and second reference element 26, 27 and calculating the position of the axes 8, 9 of the first and second distal locking hole 3, 4 of an intramedullary nail 1 by using said first and second medical image 28, 29. Then, the central axis of the drill bit 43 is adjusted subsequently to each of the axes 8, 9 of the first and second distal locking hole 3, 4 such that the roboter 42 can guide the drill bit 43 under control of the computer 40 in order to drill the holes in a bone 30 that are necessary for the insertion of locking screws in the first and second distal locking hole 3, 4.

In order to distinguish the real objects, their virtual geometric representations and the various images achieved by projecting the respective object onto the image plane the following denotation is used:

Real objects (FIGS. 1 and 2):
Intramedullary nail 1
Longitudinal axis 2
First distal locking hole 3
Second distal locking hole 4
First axis of first distal locking hole 8
Second axis of second distal locking hole 9
Distal part 5 of the intramedullary nail 1
Intersection curve 12
Virtual objects in the geometric representation (FIGS. 3 and 4):
Virtual intramedullary nail 1'
Virtual longitudinal axis 2'
Virtual first distal locking hole 3'
Virtual second distal locking hole 4'
Virtual first axis 8'
Virtual second axis 9'
Virtual distal part 5' of the virtual intramedullary nail 1'
Virtual intersection curve 12'
Objects projected onto the image plane 24 (FIGS. 5 and 7):
Pictorial intramedullary nail 1"
Pictorial longitudinal axis 2"
Pictorial first distal locking hole 3"
Pictorial second distal locking hole 4"
Pictorial first axis of pictorial first distal locking hole 8"
Pictorial second axis of pictorial second distal locking hole 9"
Pictorial distal part 5 of the pictorial intramedullary nail 1"

Figure 2:
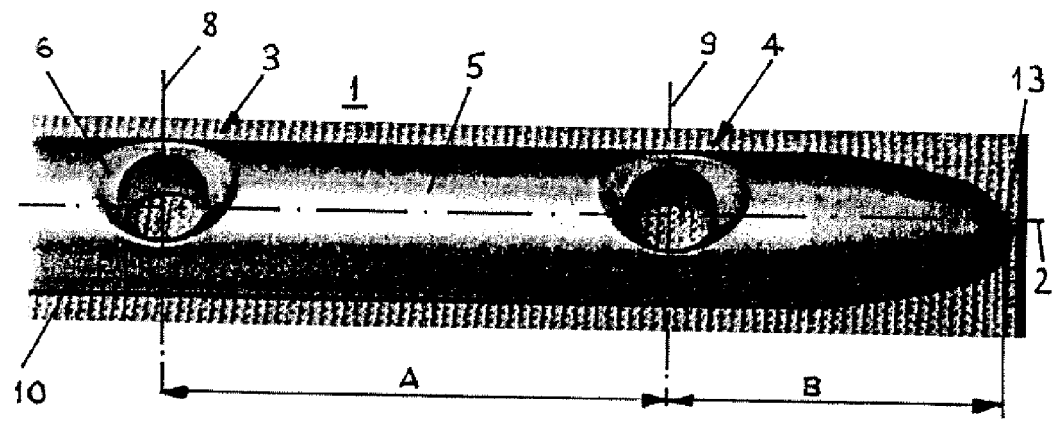
FIG. 2 illustrates a perspective view of the distal part of an intramedullary nail to be used with the embodiment of the device of FIG. 1.

In the following the preferred embodiment is elucidated with reference to FIGS. 1 to 7. The method for computer assisted distal locking of intramedullary nails essentially comprises the steps of:

a) establishing a virtual geometric representation (FIG. 3) of at least the distal part 5 of an intramedullary nail 1 comprising a first and a second distal locking hole 3,4 (FIG. 2):

As shown in FIG. 2 the first and second distal locking holes 3,4 are arranged with their axes 8,9 being parallel and at a distance A between each other. The second distal locking hole 4 which is closer to the tip 13 of the intramedullary nail 1 is located at a distance B from the tip 13. The first and second distal locking hole 3,4 are circular cylindrical and each comprise conical countersinkings 6 at its two ends running into the peripheral surface 10 of the intramedullary nail 1 (conical countersinkings 6 at the bottom side of the intramedullary nail 1 not shown).

Figures 5, 6:
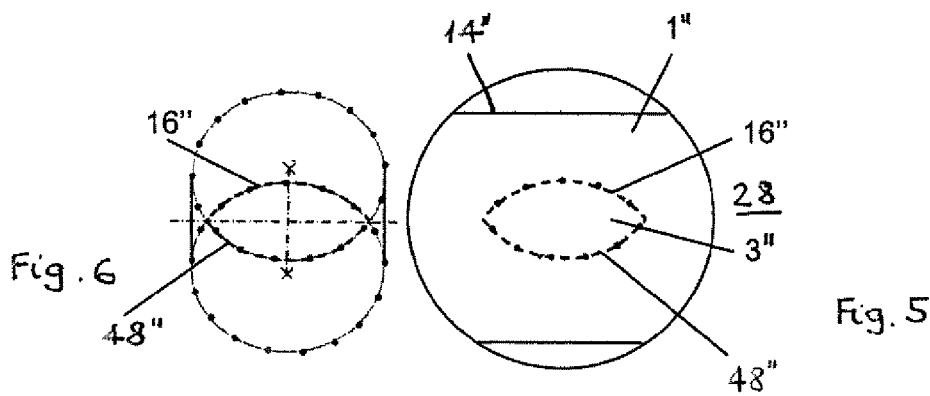
FIG. 5 illustrates a schematic representation of an essentially medio-lateral medical image.
FIG. 6 illustrates a graphic representation of the first distal locking hole viewed essentially parallel to its axis.
Figures 7, 8:
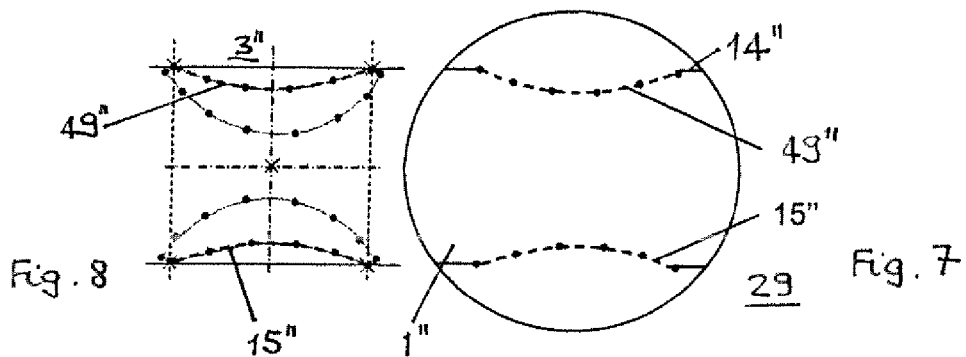
FIG. 7 illustrates a schematic representation of an essentially antero-lateral medical image.
FIG. 8 illustrates a graphic representation of the first distal locking hole viewed essentially perpendicular to its axis.

The virtual geometric representation (FIGS. 3 and 4) essentially describes a virtual distal part 5' of a virtual intramedullary nail 1' with a virtual longitudinal axis 2', a virtual first distal locking hole 3' with a virtual first axis 8' and a virtual second distal locking hole 4' with a virtual second axis 95. Thereby, a circular first virtual cylinder 50' with radius r and extending along the virtual longitudinal axis 2' represents the virtual distal part 5' of the virtual intramedullary nail 1'. The virtual first and second distal locking holes 3',4' are modelled each through a circular second virtual cylinder 11' coaxial to the first and second virtual axis 8',9' and each with a first and a second virtual truncated cone 17',51' representing the countersinks 6. The first and second virtual truncated cones 17',51' each form a virtual intersection curve 12' with the virtual peripheral surface of said first virtual cylinder 50'. This virtual geometric representation is then stored in a data store 44 of the computer 40;

b) positioning the radioscopic unit 25 in a first position with its focal line 23 adjusted with an angle between 0° and maximum 30° to the axes 8,9 of the first and second distal locking hole 3,4 i.e. extending approximately in the medio-lateral direction of the bone 30;

c) measuring the position of the first reference element 26 attached to the radioscopic unit 25 and the second reference element 27 attached to the intramedullary nail 1 or to the bone 30 with respect to a reference coordinate system by means of the position measurement device 20;

d) acquiring a first medical image 28 (FIG. 4) using the radioscopic unit 25 in said first position, said first medical image 28 showing a contour of the radiopaque distal part 5 including a pictorial outline 14" of the pictorial distal part 5" and each a lens shaped inner element with a pictorial first and second arc 16",48" representing the visible edges of the first and second distal locking hole 3,4 projected onto the image plane 24. As illustrated in FIG. 5 the pictorial first arc 16" represents the visible edge of the circular cylindrical portion of the first distal locking hole 3 which is nearer to the image plane 24, while the pictorial second arc 48" represents the visible edge of the circular cylindrical portion of the first distal locking hole 3 which is remote of the image plane 24;

e) positioning the radioscopic unit 25 in a second position with its focal line 23 adjusted with an angle between 60° and 90° to the axes 8,9 of the first and second distal locking hole 3,4 i.e. extending approximately in the antero-posterior direction of the bone 30;

e) measuring the position of the first reference element 26 attached to the radioscopic unit 25 with respect to a reference coordinate system by means of the position measurement device 20;

f) acquiring a second medical image 29 (FIG. 6) using the radioscopic unit 25 in said second position, said second medical image 29 showing a contour of the radiopaque distal part 5 including the pictorial outline 14" of the pictorial distal part 5", said outline 14" including a pictorial first and second intersection curve 15",49" representing the visible edges of the first and second distal locking hole 3,4 projected onto the image plane 24. As illustrated in FIG. 7 the pictorial first intersection curve 15" represents the visible edge of the countersinking 6 (FIG. 2) of the first distal locking hole 3 which is remote the image plane 24, while the pictorial second intersection curve 49" represents the visible edge of the countersinking 6 of the first distal locking hole 3 which is nearer to the image plane 24;

g) computing the position of the longitudinal axis 2 of the distal part 5 of the intramedullary nail 1 using said first and second medical image 28,29 and said virtual geometric representation by means of the computer 40 using the inventive algorithm;

h) computing the positions of the axes 8,9 of the first and second distal locking hole 3,4 using said first and second medical image 28,29 by means of the computer 40 in a manner that said contours visible in said first and second medical image 28,29 are matched with said virtual geometric representation by means of the computer 40 using the inventive algorithm;

i) transferring information related to the positions of the distal part 5 and the first and second distal locking hole 3,4 from a central processing unit of the computer 40 to an external guide means 41 for drilling a hole in the bone 30 which is aligned with said at least one distal locking hole 3 by means of the computer 40, whereby j) said pictorial outline 14" and said pictorial first and second arc 16",48" visible in said first medical image 28 and said pictorial outline 14" including said pictorial first and second intersection curves 15";49" visible in said second medical image 29 are matched with the virtual geometric representation by means of the computer 40 under step h).

The inventive approach for an automatic recovery of the distal locking holes of an intramedullary nail including the mathematical algorithm is described in more detail below:

In the following description for terms frequently repeated the following abbreviations are used with reference to the above description and the figures:

Model: virtual geometric representation of distal part of IMN

IMN: intramedullary nail 1 (real, virtual geometric representation and pictorial)

DLH: distal locking holes 3, 4 (real, virtual geometric representation and pictorial)

Image or fluoroscopic image: medical images 28, 29, particularly

ML image: first medical image 28 (focal line 23 adjusted approximately in the medio-lateral direction of the bone)

AP image: second medical image 29 (focal line 23 adjusted approximately in the antero-posterior direction of the bone)

A-COS$_k$: reference coordinate system 36 defined through a first reference element 26 attached to the radioscopic unit 25

P-COS: local coordinate system 35 defined through a second reference element 27 attached to the intramedullary nail 1 or to the femur 33

Figure 3:
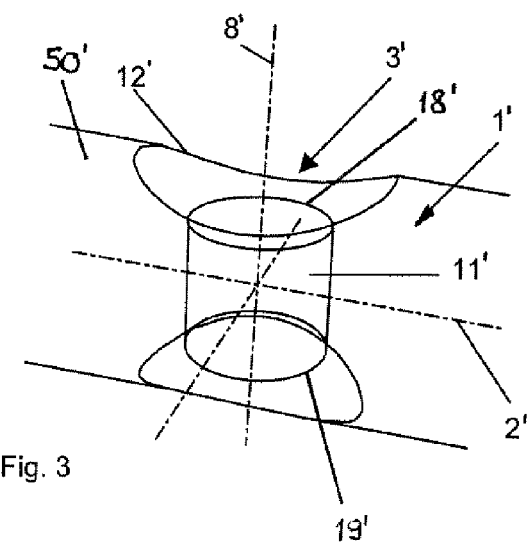
FIG. 3 illustrates a perspective graphic representation of the virtual geometric representation of the preferred embodiment of the invention.

C'uvw: second local coordinate system 38 is established by taking the intersection point c between the axis 8, 9 of the DLH and the longitudinal axis 2 of the IMN as the origin, the longitudinal axis 2 of the IMN as the u axis, and the axis 8, 9 of the DLH as the v axis (see FIG. 3 for details)

First respectively second medical image 28, 29: image S$_k$

C-arm or fluoroscope: radioscopic unit 25

Overview:

Input: two fluoroscopic images, one acquired from the medial-lateral direction and the other acquired from anterior-posterior direction of the patient 1. Calibration of input fluoroscopic images and distortion corrections Compute the camera intrinsic and extrinsic parameters as well as image undistortion maps for correcting distortions of both images 2. Stage1: nail detection 2.1 Image feature extraction: Apply Canny edge detector to both images to extract "raw" edge pixels 2.2 Initialization: Apply Principal Component Analysis (PCA) to the edge pixel set in each image to calculate the major axis of detected edge pixels in each image. Then the initial nail axis is obtained by calculating the intersection line of back-projection planes of the major axes 2.3 Nail axis estimation: Combine the IBMPP algorithm with RANSAC paradigm to fit a cylinder model with known radius to both images and estimate nail axis based on the fitting result 3. Stage 2: recovery of holes 3.1 Distal locking hole identification and image feature extraction with sub-pixel accuracy: First the sub-images that contains the hole projections are extracted. Then, cubic B-splines are employed to interpolate these sub-images to a higher resolution. Finally, Canny edge detector is applied to these high resolution sub-images to extract the edge pixels of hole projections in both images 3.2 Initialization: Find an initial transformation between the local coordinate system of the distal locking hole model and the patient reference coordinate system 3.3 X-ray projection simulation: Extract the projected silhouette of the hole model in both images Recovery of hole: Combine the IBMPP algorithm with genetic algorithm to fit the model of the hole to both images and to estimate the pose of the hole Detailed Description of Inventive Two-Stage Approach for Recovery of the Distal Locking Holes:

Image Calibration and Geometric Models 1.1. Image Calibration

In reality, the proximal fragment 31 of a bone 30, the distal fragment 32 of a bone, e.g. a femur, and the intramedullary nail 1 may be treated as three rigid bodies and registered independently. The rigid transformations between these three rigid bodies can be trivially obtained from a navigator such as a position measurement device 20, e.g. an optoelectronic tracker, a magnetic tracker, or even a medical robot [10]. Here it is assumed that the fractured femur 33 has already been reduced and the proximal fragment 31 and distal fragment 32 are kept fixed relative to each other at the time of image acquisition. We also assume that the intramedullary nail 1 has been inserted till the distal end of the bone 30, e.g. femur and has been locked proximally by a screw so that the complete bone 30 and the intramedullary nail 1 can be treated as one rigid body. A local coordinate system 35 is established on this rigid body through a so-called dynamic reference base (DRB) technique. In the following description, this patient coordinate system is denoted as P-COS. Several (typically 2) fluoroscopic images S={S$_k$, k=1, 2 ... N$_S$} are then acquired from different view directions. Further, denote the reference coordinate system 36 in each C-arm shot $S_k$ as A-COS the transformations $T_k$ between P-COS and A-COS$_k$ at the acquisition time of each fluoroscopic can be obtained and recorded, which are used to co-register the $N_S$ independent fluoroscopic images. All computations now can be done in one world coordinate system P-COS.

Figure 9:
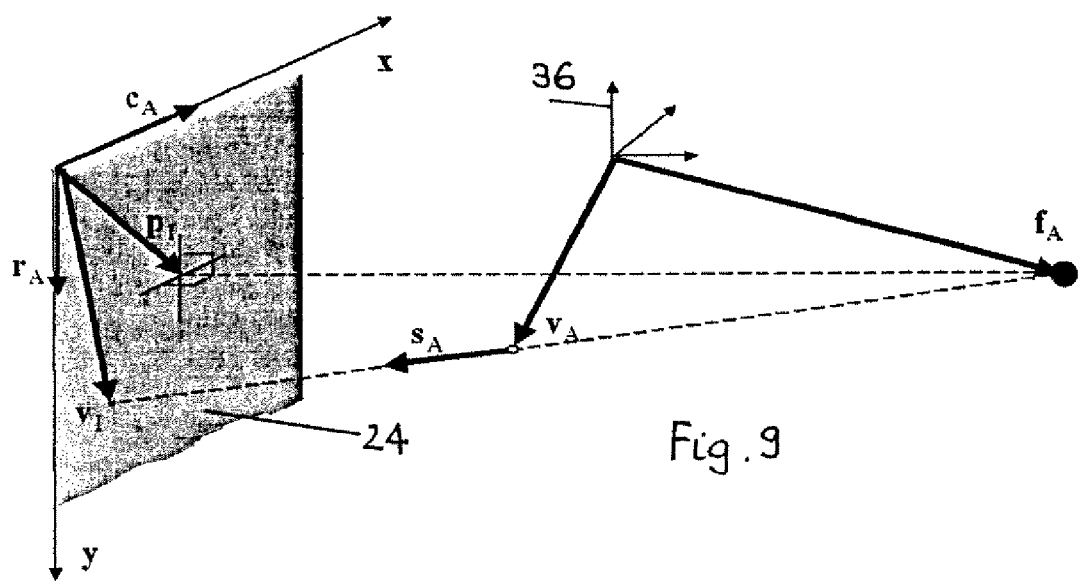
FIG. 9 illustrates a schematic representation of the image plane and the focal line of a radioscopic unit.

To relate a pixel in the 2D projection image $S_k$ to its own reference coordinate system A-COS$_k$, the acquired images have to be calibrated for physical projection properties and be corrected for various types of distortion. In the known state of the art a weak-perspective pin-hole camera model was chosen for modeling the C-arm projection, as shown in FIG. 9. The reason using a weak-perspective model is due to the fact that it is easier to calibrate than full-perspective camera model. As the model is linear, the calibration process is also better conditioned (less sensitive to noise) than the nonlinear full perspective calibration. Weak-perspective is a good approximation when the depth range of objects in the scene is small compared with the viewing distance, which is exactly the case in our application. Using such a camera model, a 2D pixel $V_I$ is related to a 3D point $V_A$ by following equations:

$$S_A = \frac{(V_A - f_A)}{\|V_A - f_A\|} \quad (1)$$

$$\begin{bmatrix} V_{I,x} \\ V_{I,y} \\ 1 \end{bmatrix} = \begin{bmatrix} c_{A,x} & c_{A,y} & c_{A,z} & p_{I,x} \\ r_{A,x} & r_{A,y} & r_{A,z} & p_{I,y} \\ 0 & 0 & 0 & 1 \end{bmatrix} \begin{bmatrix} S_{A,x} \\ S_{A,y} \\ S_{A,z} \\ 1 \end{bmatrix} \quad (2)$$

where $\|\cdot\|$ means to calculate the length of a vector and the vectors $f_A$, $r_A$, $c_A$ and $p_I$ represent the position of focal point, the vector along image row increasing direction, the vector along image column increasing direction, and the 2D position of piercing point, respectively. They are projection parameters used to describe the projection properties of the C-arm and need to be calibrated preoperatively.

Equations (1) and (2) can be used for both forward and backward projections. For example, if we want to calculate the direction $S_A$ of the forward projection ray of an image point $V_I$, an additional constraint $\|S_A\|=1$ can be used together with equation (2) to solve for it. The forward projection ray of point $V_I$ is then defined by the focal point $f_A$ and the direction $S_A$.

Distortions from pincushion effect (curved input screen) and the earth magnetic-field variations (s-shaped distortion) are different for each projection direction and hence have to be corrected for. For this purpose, a calibration grid plate consisting of equally spaced fiducial markers with known positions was designed. This plate is mounted in front of the image intensifier. For each acquired image, the real projection of these fiducial markers are detected using image processing techniques and their associated virtual projections are calculated based on equations (1) and (2). For each fiducial marker, a displacement vector that points from the real projection to the virtual projection is calculated. A bilinear local interpolation is then performed to compensate for the distortion of each image pixel. Finally, the projections of these fiducial markers are removed from the undistorted images. Details about how these image processing techniques work and how to correct the distortions are known from the state of the art.

Figure 4:
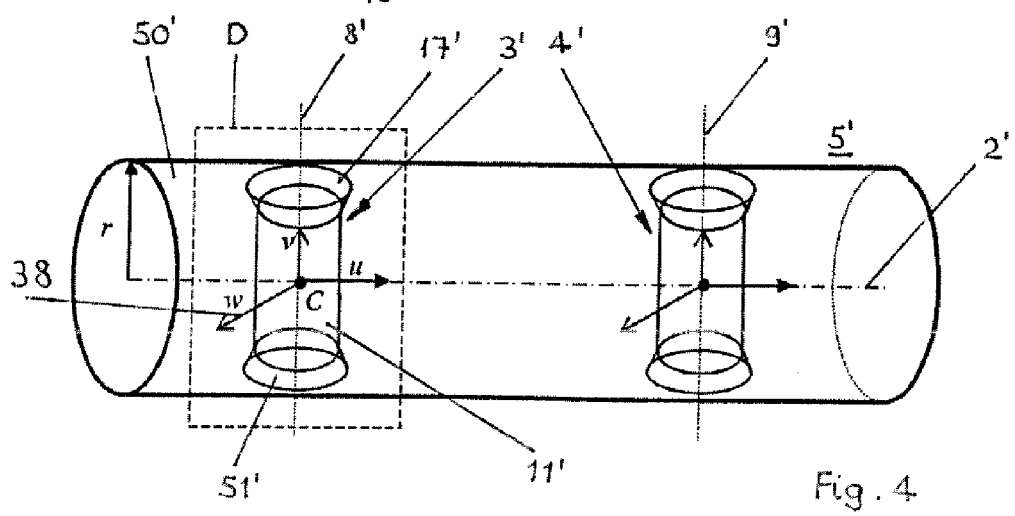
FIG. 4 illustrates a magnified graphic representation of detail D in FIG. 3.

1.2. Geometric Models (FIGS. 3 and 4)

The original idea is to directly use the Computer-Aided Design (CAD) model of the IMN. However, the shape difference between the CAD model of the IMN and the product, especially around the DLH's region, makes it an inaccurate model to be used.

The other way around is to extract the geometrical description of the distal part of the IMN directly from the product. By doing this, two advantages are gained: (1) the proposed approach becomes more generic and can be easily integrated with any type of nail, as it does not depend on the CAD model any more, which can only be obtained from the manufacturer. All required data are directly measured from the product. The modern standardized manufacturing technology makes it possible to apply the measurement from one product to all other similar product from the same manufacturer, at least from the geometrical measurement point of view; (2) it reduces the data need to be processed as there is only need to extract the data required for the inventive specific algorithm.

To this end, the distal part of IMN containing the two DLH's, which is what is of interest, is modeled as a cylinder with known radius, which can be directly measured from the IMN using a caliber or accurately extracted from its product information.

In regards to the model of DLH, most of existing prior art treated it as a cylinder with known radius and height. This simplified model prevented them from using the information provided by the AP image. For example in US-A 2005/0027304 LELOUP, only the ML image is used to recover the pose of the DLH, though both AP and ML images were used to detect the IMN and to estimate the nail axis. It is considered that the robustness and accuracy of pose recovery can be improved by accurately modeling the distal locking hole.

FIG. 4 shows the inventive model for DLH. It is a combination of an inner cylinder model with two cone trapezoid openings. For the purpose of X-ray projection simulation, it is accurate enough to describe this model by two outer intersection curves between the DLH and the IMN, and two end circles of the inner cylinder, as shown in FIG. 4. The two outer intersection curves are used to simulate silhouette projection of the distal locking hole from AP direction and the two end circles of the inner cylinder are used to simulate silhouette projection from ML direction.

To obtain the coordinates of those points (visualized as dots in FIGS. 6 and 8) used to describe this model, a local coordinate system C'uvw is established by taking the intersection point C between the axis of the DLH and the axis of the IMN as the origin, the axis of the IMN as the u axis, and the axis of the DLH as the v axis (see FIG. 4 for details). The coordinates of those points expressed in this local coordinate system can be directly measured from the nail using a caliber, thanks to the symmetrical property of the DLH; or extracted from the engineering drawings of the nail, if they are available.

1. The Iterative Best Matched Projection Point (IBMPP) Algorithm

Pose estimation is a fundamental problem in machine vision. It estimates the relative pose (position and orientation) between a 3D object and its 2D image from a set of feature correspondences. With an appropriate choice of reference frame, the pose estimation can be viewed as either determining the camera pose with respect to a known object or as estimating the object pose with respect to a known camera. The case reported in this paper belongs to the latter category.

Model-based pose estimation works by incorporating prior knowledge, specifically geometric knowledge, into pose estimation process. The estimation is formulated as a constrained nonlinear optimization problem that can be solved by Levenberg-Marquardt non-linear optimization method or by Newton's method. The existing approaches, pioneered by Lowe include five steps: 1) Project model into images; 2) Find a set of image features to match to projection of model and compute mismatch errors at these image features; 3) Compute partial derivatives and Hessian matrix of mismatches relative to pose parameters; 4) Adjust pose parameters according to Newton's method; 5) Repeat until convergence. As Newton-based recursions are used, these approaches have a quadratic rate of local convergence. However, they also rely on a good initial pose estimate and might converge to a local minimum.

The algorithm proposed in this paper is inspired by Wunsch and Hirzinger and Guéziec et al. Instead of solving a nonlinear optimization problem, Wunsch and Hirzinger report an iterative inverse perspective matching (IIPM) algorithm for registration of CAD-models to images. This algorithm uses the projection rays as a guide to determine the pose of the (CAD) models in an image and is composed of two successive steps. The first of these two steps determines correspondences between image features and CAD model data, while the second computes the rigid body transformation that minimizes the displacement of matched features. The model image matching is then iteratively refined following the idea of the iterative closest point algorithm. Guéziec et al. further extend this method by extracting apparent contour from the triangle mesh description of the model to allow for registration of not just simple CAD-models but also complex anatomical structures to the images. A drawback of all these methods is that outliers introduced in the feature extraction phase can not be eliminated subsequently. To address this drawback, an explicit 2D matching step is proposed in our approach to eliminate part of the outliers. This is also the reason why we call the new algorithm as Iterative Best Matched Projection Point (IBMPP) algorithm.

More specially, the IBMPP algorithm is defined as follows. Let's denote the pose parameters to be optimized as $\{\lambda_j\}$. Further denote $E_k$ be a set of $N_k$ detected 2D edge pixels $\{e_k^1, e_k^2, \ldots, e_k^{N_k}\}$ from image $S_k$. Let M be a set of $N_M$ 3D points $\{m^1, m^2, \ldots, m^{N_M}\}$ which is defined in the local coordinate system of the object and is used to describe the model of the object. Given initial values of all pose parameters $\{\lambda_j^{(0)}\}$, an initial rigid transformation $T(\{\lambda_j^{(0)}\})$ between the local coordinate system of the object model and the world coordinate system P-COS can be computed. All model points $\{m^1, m^2, \ldots, m^{N_M}\}$ defined in their local coordinate system can then be transformed to P-COS as $\{m^{1,(0)}, m^{2,(0)}, \ldots, m^{N_M,(0)}\}$. Let $\{m^{1,(t-1)}, m^{2,(t-1)}, \ldots, m^{N_M,(t-1)}\}$ be those points defined in P-COS at iteration step t−1. Now in the iteration step t, we perform following steps:

Model projection step: In this step, we project model to each image. Let $P_K^{(t-1)}$ be a set of $N_P$ 2D projection points $\{p_K^{1,(t-1)}, p_K^{2,(t-1)}, \ldots, p_K^{N_P,(t-1)}\}$ obtained by simulating X-ray projection of 3D model into the image $S_K$. Normally $N_P \ll N_M$. Thus, for each 2D projection point $p_K^{i,(t-1)}$, we know its associated 3D model point 2D matching step: In each image, find the best matched 2D point pairs $\{(e_K^i, p_K^{i,(t-1)})\}$ according to certain similarity metric, where $e_K^i$ is a detected 2D edge pixel and $p_K^{i,(t-1)}$ is a 2D model projection point.

3D-2D correspondence step: Calculate the forward projection ray $BP_K^i$ of each 2D edge pixel $e_K^i$ in the best matched point pairs $\{(e_K^i, p_K^{i,(t-1)})\}$ Then for each ray $BP_K^i$, calculate a 3D point pair $PP_K^{i,(t-1)} = (be_K^{i,(t-1)}, m^{i,(t-1)})$, where $be_K^{i,(t-1)}$ is a point on the line $BP_K^i$ that is closest to the 3D model point $m^{i,(t-1)}$ of the model projection point $p_K^{i,(t-1)}$.

Pose estimation step: For all calculated point pairs $PPS^{(t-1)} = \{PP_k^{i,(t-1)}\}$, find an optimal local solution of all pose parameters $\{\lambda_j^{(t-1)*}\}$ by solving following minimization problem $$\min_{\{\lambda_j^{(t-1)*}\}} \sum_{k,i} \|be_k^{i,(t-1)} - T(\{\lambda_j^{(t-1)}\}) \cdot m^{i,(t-1)}\|^2 \quad (3)$$

And then use the estimated parameters to calculate the rigid transformation $T(\{\lambda_j^{(t-1)*}\})$ Pose updating step: Update the pose of all model points $\{m^{1,(t-1)}, m^{2,(t-1)}, \ldots, m^{N_M,(t-1)}\}$ by $T(\{\lambda_j^{(t-1)*}\})$ to $\{m^{1,(t)}, m^{2,(t)}, \ldots, m^{N_M,(t)}\}$.

Repeat until all pose parameters converge

2. Detailed Description of the Proposed Approach

The proposed IBMPP algorithm is used in both stages to optimize the solution from the initialization. But due to the different contexts in these two stages, the IBMPP algorithm is combined with different strategies to robustly find the optimal solution for each stage. In the first stage, where we try to robustly detect and accurately estimate the axis of the distal part of the IMN from complex backgrounds, the main task is to eliminate the effect from outliers. This is handled by Random Sample Consensus (RANSAC) paradigm. While in the second stage, where the projection contours of the DLH's can be accurately extracted using the knowledge obtained in the first stage, the task is to find the optimal solution starting from a roughly estimated position. To this end, a conventional genetic algorithm is used together with the IBMPP algorithm. In the following description, we pay more attention to the details of individual step for each stage, which include image feature extraction, initialization, projection of model, 2D matching, pose estimation, and the strategy to further improve the robustness of the IBMPP algorithm.

3.1. Stage1: Nail Detection

A. Image Feature Extraction

Observing the significant intensity difference between the nail projections and the projections of femur, we apply a Canny edge detector with hysteresis to all the fluoroscopic images to extract the "raw" edge pixels. The "raw" edge data are a combination of the valid nail edges and the false edges from projections of the nail cone tip, the locking holes, image noise, and the patient reference fixation device.

B. Initialization

Figure 10:
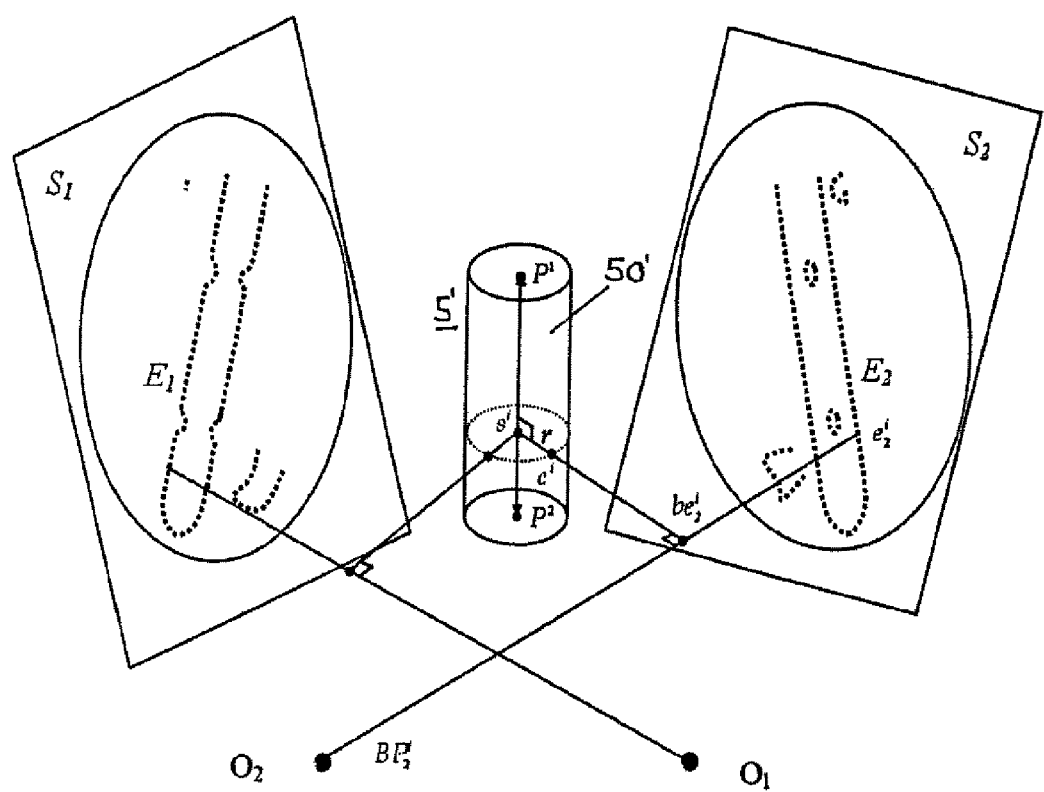
FIG. 10 illustrates a schematic representation used to describe the inventive algorithm.

The distal part of the IMN is modeled as a cylinder with known radius r. Let's call it the nail cylinder (NC) in the following description and parameterize it with parameters $[l,x,y,z,\alpha,\beta,\gamma]$, where l, [x,y,z], and $[\alpha,\beta,\gamma]$ are the length of the NC, the position of its centroid, and the orientation of its axis. These parameters are initialized as follows (see FIG. 10). We first calculate the major axis $AE_k$ of the edge point set $E_k$ by applying principal component analysis (PCA) to $E_k$. Following the same notation in [9], we also call the back-projection plane of the major axis $AE_K$ in P-COS the principal plane of image $S_k$. The initial axis of the NC is then obtained by computing the intersection line between two principal planes, which gives the initial parameters $[l^0, x^0, y^0, z^0, \alpha^0, \beta^0, \gamma^0]$ in P-COS, as shown by FIG. 10.

C. Model Projection

The simulated X-ray projection of the NC is represented by the silhouette projections of its shaft, which are two parallel lines. These two lines are sampled according to the image resolution to create a set of model projection points.

D. 2D Matching

In each image and for each model projection point, we first try to find the closest image feature to set up a 2D matched point pair $(e_K^i, p_K^i)$, where $e_K^i$ is a detected 2D edge pixel and $p_K^i$ is a model projection point. Due to the existence of outliers, it is possible that some of the model projection points are matched to outliers. To eliminate part of the false matching, we take advantage of the knowledge that the silhouette projections of a cylinder shaft are lines, i.e., there should be also a line around the matched edge pixel. Thus, for each 2D matched point pair $(e_K^i, p_K^i)$, we put a mask of size m×m (in our experiments, m=11) pixel$^2$ around $e_K^i$. If the number of detected edge pixels inside this window is too small (e.g., <5) or too big (e.g., >20), we will drop this matched point pair. Otherwise, we apply a principal component analysis to all edge pixels found inside this window, and then count the number of the edge pixels that are close enough (e.g., <0.2 pixel) to the estimated principal axis. If the number is too small, we will also drop this matched point pair. The rest of the matched point pairs are then used as the input for the IBMPP algorithm to iteratively update the pose of the NC. By doing this, we can greatly reduce the outlier matching rate.

E. Pose Estimation

Given a set of matched 2D point pairs $\{(e_K^i, p_K^{i,(t-1)})\}$ and the pose parameters $[l^{(t-1)}, x^{(t-1)}, y^{(t-1)}, z^{(t-1)}, \alpha^{(t-1)}, \beta^{(t-1)}, \gamma^{(t-1)}]$ of the NC at step t−1, we first compute the two ends of the axis of the NC as follows.

$$\begin{cases} P^{1,(t-1)} = [x^{(t-1)}, y^{(t-1)}, z^{(t-1)}]^T + [\cos(\alpha^{(t-1)}), \\ \cos(\beta^{(t-1)}), \cos(\gamma^{(t-1)})]^T \cdot (l^{(t-1)}/2) \\ P^{2,(t-1)} = [x^{(t-1)}, y^{(t-1)}, z^{(t-1)}]^T - [\cos(\alpha^{(t-1)}), \\ \cos(\beta^{(t-1)}), \cos(\gamma^{(t-1)})]^T \cdot (l^{(t-1)}/2) \end{cases} \quad (4)$$

Then, for each 2D matched point pair $(e_K^i, p_K^{i,(t-1)})$, we calculate a 3D point pair $(be_k^i, s^i)$, where $be_k^i$ and $s^i$ are the two 3D points on the forward projection ray of $e_k^i$ and on the axis $p^{1,(t-1)} p^{2,(t-1)}$ of the NC, respectively, and give the shortest distance between these two lines, as shown in FIG. 7.

And for each 3D point pair $(be_k^i, s^i)$, we do a further calculation to get another 3D point pair $PP_k^{i,(t-1)} = (be_k^i, c^i)$, where $$c^i = s^i + \frac{(be_k^i - s^i)}{\|be_k^i - s^i\|} \cdot r \quad (5)$$

The parameters of the NC are then updated in two steps as follows.

Step 1: Keep $[x^{(t-1)}, y^{(t-1)}, z^{(t-1)}, \alpha^{(t-1)}, \beta^{(t-1)}, \gamma^{(t-1)}]$ constant, update the length $l^{(t-1)}$ to $l^{(t)}$.

To achieve this, we first find a subset of computed 3D matched pairs $\{(be_k^j, c^j)\}$ and their associated point pairs $\{(be_k^j, s^j)\}$ by requiring:

$$\|be_k^j - c^j\| < \epsilon \quad (6)$$

where $\epsilon$ is a pre-selected distance threshold.

Thus, each point $s^j$ can be expressed as:

$$s^j = [x^{(t-1)}, y^{(t-1)}, z^{(t-1)}]^T + [\cos(\alpha^{(t-1)}), \cos(\beta^{(t-1)}), \cos(\gamma^{(t-1)})]^T \cdot \tau^j \quad (7)$$

where $\tau^j$ is the distance between $s^j$ and the centroid of the NC.

We then try to find out the range $(\tau^{min}, \tau^{max})$ of all $\tau^i$ and update $l^{(t)}$ as $(\tau^{max} - \tau^{min})$.

Step 2: Keep $l^{(t)}$ constant, update $[x^{(t-1)}, y^{(t-1)}, z^{(t-1)}, \alpha^{(t-1)}, \beta^{(t-1)}, \gamma^{(t-1)}]$ to $[x^{(t)}, y^{(t)}, z^{(t)}, \alpha^{(t)}, \beta^{(t)}, \gamma^{(t)}]$.

To achieve this, the method proposed in Veldpaus et al. is applied to the estimated paired-point set $\{PP_k^{i,(t-1)}\}$ to compute a rotation matrix $R^{(t-1)}$ and a translation vector $tr^{(t-1)}$. The parameters $[x^{(t-1)}, y^{(t-1)}, z^{(t-1)}, \alpha^{(t-1)}, \beta^{(t-1)}, \gamma^{(t-1)}]$ of the NC are then updated to $[x^{(t)}, y^{(t)}, z^{(t)}, \alpha^{(t)}, \beta^{(t)}, \gamma^{(t)}]$ by the computed rigid transformation.

F. Strategy to Further Improve the Robustness of the IBMPP Algorithm

In medical applications, robustness is always an important topic. Although the effects of outliers have already been partially eliminate by using an explicit 2D matching step and a robust 3D-3D registration, we need a strategy to further improve the robustness of the IBMPP algorithm. In our approach, this is handled by the Random Sample Consensus (RANSAC) paradigm. The advantage of combining the IBMPP algorithm with the RANSAC paradigm is that they are compensate for each other. The property of partial elimination of outliers of the IBMPP algorithm reduces the outlier rate such that the required sampling times of the RANSAC paradigm is also reduced, while the RANSAC paradigm can be used to further improve the robustness of the IBMPP algorithm.

To determine sampling parameters such as the number of sampling points and the trial number, we have done a Monte Carlo simulation. Based on this simulation, we have chosen the number of sampling points as 10 and the sampling trial times as 20.

3.2. Stage 2: Recovery of DLH's

A. DLH Edge Detection

The silhouette projection of the shaft of the estimated NC into each image defines a rectangle area. The projections of the DLH's in each image are located inside the associated rectangle area. Our task in this step is to extract the sub-images containing the projections of the DLH's and then to extract the edge pixels belonging to the boundaries of the projections of the DLH's To determine those edge pixels of DLH's in ML images, the method reported in [9] is modified for our purpose A parallelepiped window, whose sizes are equal to the width of the rectangle area, is swept along the projected line of the axis of the NC to find two locations which contain the maximum number of edge pixels and whose distance is greater than a pre-selected distance threshold T (e.g. the width of the rectangle area). But unlike a known method, no ellipse fitting is required, as our approach works directly on the extracted edge pixels.

The detected edge pixels of the DLH's in ML image are helpful to locate a similar square window in AP image as follows. In each detected location in ML image, the centroid of the detected edge pixels inside the square window is calculated. Then a point on the axis of the estimated NC, which is closest to the forward projection ray of the centroid, is computed. Its projection into the AP image defines the location of a square window in AP image.

Now two sub-images are extracted from each image, which contain the projections of DLH's. We apply a Canny edge detector to these two sub-images to extract the edges of the projections of DLH's. All newly detected edge pixels inside the square windows in ML image are chosen as the candidate edge pixels of DLH's. In AP image, a further step is performed to select only those edge pixels whose distances to the closest silhouette projection (a line) of the estimated NC are greater than certain pixels (e.g. 10 pixels).

Observing the wide variations of the nail deformation, we apt for recovering the poses of the two DLH's one by one. In the following descriptions, we concentrate on pose recovery of the first hole. The same principle is applied to the second one taking the orientation of the recovered axis of the first hole as the initial orientation of its axis.

B. Initialization

The task in this step is to find the initial transformation between the local coordinate system C'uvw of the geometrical model of the DLH and P-COS. This is solved by computing the initial position of coordinate origin C and the initial orientations of each coordinate axis in P-COS.

The coordinate origin c is defined as the intersection point between the axis of the DLH and the axis of the distal part of the nail To find the initial position of c in P-COS, the centroid of the detected edge pixels of the distal locking hole in ML image is first computed. The initial position of C is then calculated by find a point on the axis of the estimated NC that is closest to the forward projection ray of the centroid.

The initial orientations of coordinate axis u, v, w in P-COS are estimated as follows. According to the definition of C'uvw, the axis of the estimated NC is exactly the u axis. The initial w axis is defined as the cross product of the nail axis and the normal vector of ML imaging plane (the negative direction of the piercing line in FIG. 9). The initial v axis is then obtained by calculating the cross product of w and u, which is taken as the initial estimation of the axis of the DLH.

The initial transformation between the local coordinate system C'uvw of the geometrical model of the DLH and the patient reference coordinate system P-COS then is $$\text{translation}_{ini} = \begin{bmatrix} C_x \\ C_y \\ C_z \end{bmatrix} \quad \text{Rotation}_{ini} = \begin{bmatrix} u_x & v_x & w_x \\ u_y & v_y & w_y \\ u_z & v_z & w_z \end{bmatrix} \quad (8)$$

Now all points defined in the local coordinate system of the geometrical model of the DLH can be transformed to C-COS by this initial transformation. In the following description, we assume that all points used to describe the geometrical model of the DLH have already been transformed to P-COS.

C. Model Projection

A key step for a successful model-based pose recovery is to accurately simulate X-ray projections, i.e., to extract the projection silhouettes of the geometrical model of the DLH. As the nail is made of metal, the X-ray can not pass through it except at the sites of openings. Based on this principle, the simulated projections of the geometrical model of the DLH into ML and AP images are extracted using different geometrical descriptions.

The simulated projections into ML image are extracted as shown by FIGS. 5 and 6. The complete procedure is divided into two steps and only points on the two end circles of the inner cylinder of the geometrical model are involved in the computation. First, the centers of the two end circles as well as all points on these two circles are projected into the ML image. Second, the valid projections into ML image are found as follows. Let's denote the two projected centers as $O_1$ and $O_2$. If $O_1$ and $O_2$ are very close, i.e., the distance between them is less than one pixel, we will choose all projected points on both circle as the silhouette projection of the DLH into ML image. If not, we then calculate the perpendicular bisector of the line $O_1O_2$. This bisector line separates the projected points on each circle into two sets, as shown by FIGS. 5 and 6. One set of points are on the same side of the bisector line as the projected center does, and the other are on the opposite site. The silhouette projections of the DLH into ML image are then extracted by keeping the set of points that are on the opposite sides of the projected centers.

The simulated projections into AP image are extracted as shown by FIGS. 7 and 8. The complete procedure is also divided into two steps and only points on the two outer intersection curves of the geometrical model are involved in the computation. First, we calculate the projections of following objects in the AP image, including all measured points on the two outer curves, the center c of the geometrical model of the DLH, and the axis of the estimated NC. We also need to calculate the silhouette projection of the NC shaft in AP image, which is represented by two lines along the longitudinal edges of the nail. We then find the valid projections based on their visibilities. Let's denote the projection of the center C as $O_C$. A line passing $O_C$ and being perpendicular to the projection (a line) of the estimated NC axis separates the projected points on each outer curve into two sub-sets. In each sub-set of points, we find the point closest to the nearer silhouette projection of the estimated NC shaft. Passing through this point and being perpendicular to the nearer silhouette projection of the estimated NC shaft can we define another line. This line further separates those projected points in the sub-set into three groups: (a) points that are at the same side as $O_C$ but closer to the silhouette projection of the NC shaft; (b) points that are at the same side as $O_C$ but further away from the silhouette projection of the NC shaft; and (c) points that are at the opposite side of $O_C$. Finally, the silhouette projections of DLH into AP image are extracted by keeping all points of the first group.

D. 2D Matching

As we require that there is no outlier projection at the site of DLH projection, the nearest-neighbor relationship is utilized to set up the 2D matched point pairs in both images.

E. Pose Estimation

Taking the directions of the possible bending forces applied during insertion and the fact that nail is made of metal into consideration, we assume that the axis of the DLH is still coplanar with the axis of the distal part of the IMN after insertion. Thus, the problem to estimate the pose of the DLH in P-COS is changed to find the rotation angle θ and the translation distance de of the geometrical model of the DLH along the axis of the estimated NC so that the simulated X-ray projection of the DLH can be fitted to its real X-ray projection. Let's assume the orientation of the axis of the estimated NC is $(n_x, n_y, n_z)$. The constrained transformation around the axis of the NC could be written as:

$$rot(\theta, d_t) = \begin{bmatrix} n_x^2 + & n_x n_y (1-\cos(\theta)) - & n_x n_z (1-\cos(\theta)) + \\ (n_y^2 + n_z^2)\cos(\theta) & n_z \sin(\theta) & n_y \sin(\theta) \\ n_x n_y (1-\cos(\theta)) + & n_y^2 + & n_y n_z (1-\cos(\theta)) - \\ n_z \sin(\theta) & (n_z + n_x^2)\cos(\theta) & n_x \sin(\theta) \\ n_x n_z (1-\cos(\theta)) - & n_y n_z (1-\cos(\theta)) + & n_z^2 + \\ n_y \sin(\theta) & n_x \sin(\theta) & (n_x^2 + n_y^2)\cos(\theta) \end{bmatrix} \text{ and} \quad (9)$$

$$trans(\theta, d_t) = \begin{bmatrix} t_x \\ t_y \\ t_z \end{bmatrix}; \text{ where } t_x, t_y, t_z \text{ is defined as}$$

$$\begin{cases} t_x = (C_x + d_t \cdot n_x) \cdot (n_y^2 + n_z^2) - n_x \cdot ((C_y + d_t \cdot n_y) \cdot n_y + (C_z + d_t \cdot n_z) \cdot \\ n_z) + (n_x \cdot ((C_y + d_t \cdot n_y) \cdot n_y + (C_z + d_t \cdot n_z) - (C_x + d_t \cdot n_x) \cdot \\ (n_y^2 + n_z^2))\cos(\theta) + ((C_y + d_t \cdot n_y) \cdot n_z - (C_z + d_t \cdot n_z) \cdot n_y)\sin(\theta) \\ t_y = (C_y + d_t \cdot n_y) \cdot (n_x^2 + n_z^2) - n_y \cdot ((C_z + d_t \cdot n_x) \cdot n_x + (C_z + d_t \cdot n_z) \cdot \\ n_z) + (n_y \cdot ((C_x + d_t \cdot n_x) \cdot n_x + (C_z + d_t \cdot n_z) - C_y + d_t \cdot n_x) \cdot \\ (n_x^2 + n_z^2))\cos(\theta) + ((C_z + d_t \cdot n_z) \cdot n_x - (C_x + d_t \cdot n_x) \cdot n_z)\sin(\theta) \\ t_z = (C_z + d_t \cdot n_z) \cdot (n_x^2 + n_y^2) - n_z \cdot ((C_x + d_t \cdot n_x) \cdot n_x + (C_y + \\ d_t \cdot n_y) \cdot n_y) + (n_z \cdot ((C_x + d_t \cdot n_x) \cdot n_x + (C_y + d_t \cdot n_y) - C_z + d_t \cdot n_z) \cdot \\ (n_x^2 + n_y^2))\cos(\theta) + ((C_x + d_t \cdot n_x) \cdot n_y - (C_{yz} + d_t \cdot n_y) \cdot n_x)\sin(\theta) \end{cases} \quad (10)$$

Let's denote $HE_k$ as the $M_k$ detected 2D raw edge pixels $\{he_k^1, he_k^2, \ldots, he_k^{M_k}\}$; of the DLH from image $S_k$. The IBMPP algorithm is used again to find the optimal solutions of θ and $d_t$ at step t−1 as follows.

(a) Project the model of the distal locking hole to both images to extract the simulated X-ray projection using method described in section C. Let's denote the simulated X-ray projection of DLH in image $S_k$ as $PS_k$. $PS_k$ is expressed as $D_k$ 2D projected points $\{ps_k^{1,(t-1)}, ps_k^{2,(t-1)}, \ldots, ps_k^{D_k,(t-1)}\}$, and whose associated 3D model points $\{hm^{1,(t-1)}, hm^{2,(t-1)}, \ldots, hm^{D_k,(t-1)}\}$ are known (b) For each point on the extracted projection silhouettes of the distal locking hole, $ps_k^i \in PS_k$, find the closest edge pixel $he_k^i$, and then calculate a pair of points $PP_k^{i,(t-1)} = (hm^{i,(t-1)}, bhe_k^i)$, where $hm^{i,(t-1)}$ is the associated 3D model point of $ps_k^i$, and $bhe_k^i$ is the point on the forward projection ray of $he_k^i$ that is closest to $hm^{i,(t-1)}$ (c) For all calculated point pairs $PPS^{(t-1)} = \{PP_k^{i,(t-1)}\}$ find an optimal solution of $(\theta^*, d_t^*)$ by solving following minimization problem $$\min_{\theta^*, d_t^*} S(\theta, d_t) \text{ where} \qquad (11)$$

$$S(\theta, d_t) = \sum_{k,i} |bhe_k^i - (rot(\theta, d_t) \cdot hm^{i,(t-1)} + trans(\theta, d_t))|^2.$$

This minimization problem can be solved by requiring:

$$\left.\frac{\partial S(\theta, d_t)}{\partial \theta}\right|_{\substack{\theta=\theta^* \\ d_1 = d_t^*}} = 0, \text{ and } \left.\frac{\partial S(\theta, d_t)}{\partial d_t}\right|_{\substack{\theta=\theta^* \\ d_t = d_1^*}} = 0 \qquad (12)$$

In each iteration step, the changing angle $\theta^*$ calculated by above minimization is normally small (<10°). One way to speed up the computation of $\theta^*$ when solving equations (12) is to replace $\cos(\theta)$ and $\sin(\theta)$ by their approximated values of 1 and $\theta$, respectively.

(d) Update all points of the geometrical model of the DLH with the newly computed transformation $(rot(\theta^*, d_t^*), trans(\theta^*, d_t^*))$ (e) Repeat step (a)-(d) until $(\theta, d_t)$ converge.

F. Strategy to Escape from Local Convergence

The IBMPP algorithm can be regarded as a local minimum search algorithm. As in any other registration techniques, the main problem for the IBMPP algorithm is to find the global minimum of the disparity function $S(\theta, d_t)$ that may be well hidden among many poorer local minima, especially when the initialization is not so close to the global minima. In our approach, this is handled by combining a conventional genetic algorithm [19] with the proposed IBMPP algorithm. The genetic algorithm acts as a random generator for possible parameter sets that solve the minimization problem. All generated individual parameter set is then fed through the IBMPP algorithm before being rated using the disparity function. Five best ones (with the lowest value of $S(\theta, d_t)$) become the parents of next generation. The algorithm stops when the differences of the disparity function values of all five best ones are smaller than a pre-selected threshold.

While various descriptions of the present invention are described above, it should be understood that the various features can be used singly or in any combination thereof. The scope of the present invention is accordingly defined as set forth in the appended claims.

What is claimed is:

1. A method for computer assisted distal locking of intramedullary nails comprising the steps of:
A) establishing a virtual geometric representation at least of the distal part (5) of an intramedullary nail (1) comprising at least one distal locking hole (3,4);
B) acquiring a first medical image (28) using a radioscopic unit (25) with its focal line (23) adjusted at an angle between 0° and 30° of the axis (8,9) of the at least one distal locking hole (3,4), said first medical image (28) showing a contour of the radiopaque distal part (5) including a pictorial outline (14") of the pictorial distal part (5") and at least one lens shaped inner element with a pictorial first and a second arc (16",48") representing the visible edges of the at least one distal locking hole (3,4) projected onto the image plane (24);
C) acquiring a second medical image using a radioscopic unit (25) with its focal line (23) adjusted at an angle between 60° and 90° to the axis (8,9) of the at least one distal locking hole (3,4), said second medical image (29) showing a contour of the radiopaque distal part (5) including a pictorial outline (14") of the pictorial distal part (5"), said pictorial outline (14") including a pictorial first and second intersection curve (15",49") representing the visible edges of the at least one distal locking hole (3,4) projected onto the image plane (24);
D) computing the position of the longitudinal axis (2) of the distal part (5) of the intramedullary nail (1) using said first and second medical image and said virtual geometric representation by means of a computer (40);
E) computing the position of the axis (8,9) of the at least one distal locking hole (3,4) using said first and second medical image (28,29) by means of the computer (40) in a manner that said contours visible in said first and second image (28,29) are matched with said virtual geometric representation;
F) transferring information related to the positions of the distal part (5) and the at least one distal locking hole (3,4) from a central processing unit of the computer (40) to an external guide means (41) for drilling a hole in a bone (30) which is aligned with said at least one distal locking hole (3,4), whereby
G) said pictorial outline (14") and said pictorial first and second arc (16",48") visible in said first medical image (28) and said pictorial outline (14") including said pictorial first and second intersection curve (15",49") visible in said second medical image (29) are matched with the virtual geometric representation by means of the computer (40) under step E).

2. The method according to claim 1, wherein said external guide means (41) is a display (45) electronically connected computer (40).

3. The method according to claim 1, wherein said external guide means (41) is a computer controlled drive for automatically adjusting a drill guide.

4. The method according to claim 1, wherein said external guide means (41) is a surgical roboter (42) automatically drilling the hole in a bone (30).

5. Device for computer assisted distal locking of an intramedullary nail comprising:
a) a computer (40) with a data store;
b) a position measurement device (20) electronically connected to the computer (40) for measuring the position of at least one reference element (26,27);
c) a radioscopic unit (25) with a focal line (23) and a first reference element (26), said radioscopic unit (25) allowing acquisition of a first and second medical image (28, 29) of at least a distal part (5) of an intramedullary nail (1) including at least a first and a second distal locking hole (3,4) with an axis (8,9) each, said first and second medical image (28,29) being acquired with the focal line (23) being transverse to the intramedullary nail (1) and with the focal line (23) adjusted at an angle between 0° and 30° to the axes (8,9) of the first and second distal locking hole (3,4) for the first medical image (28), respectively with an angle between 60° and 90° to said axes (8,9) for the second medical image (29);

d) a second reference element (27) connected with the intramedullary nail (1) or with a bone (30) in which the intramedullary nail (1) is implanted;

e) a roboter (42) comprising a drill bit (43) with a central axis allowing the drilling of holes necessary for the distal locking of an intramedullary nail (1), the position of said holes being previously calculated by means of said computer (40) through referencing the first and second reference element (26,27) and calculating the position of the axes (8,9) of the first and second distal locking hole (3,4) of an intramedullary nail (1) using said first and second medical image (28,29), whereby the central axis of the drill bit (43) is adjusted subsequently to each of the axes (8,9) of the first and second distal locking hole (8,9) such that the roboter (42) can guide the drill bit (43) under control of the computer (40) in order to drill the holes in a bone (30) that are necessary for the insertion of locking screws in the first and second distal locking hole (3,4), whereby f) said computer (40) is suitably programmed for an automatic recovery of a first and a second distal locking hole (3,4) of an intramedullary nail (1) by means of a two-stage approach, wherein i) in a first stage the position of the longitudinal axis (2) of the distal part (5) of an intramedullary nail (1) is computed using said first and second medical image (28,29) and a virtual geometric representation of the distal part (5) of an intramedullary nail (1); and ii) in a second stage the position of the axes (8,9) of the first and second distal locking hole (3,4) of an intramedullary nail (1) is computed by combining a genetic algorithm with a local minimum search algorithm using said first and second medical image (28, 29).

* * * * *